United States Patent [19]

Junek et al.

[11] Patent Number: 4,785,113

[45] Date of Patent: Nov. 15, 1988

[54] 2,4-DICHLORO-3,5,6-TRIMETHYLPYRIDINE

[75] Inventors: Hans Junek; Martin Mittelbach; George Uray; Hans-Werner Schmidt, all of Graz, Austria

[73] Assignee: Aktiebolaget Hassle, Sweden

[21] Appl. No.: 908,355

[22] Filed: Sep. 17, 1986

[30] Foreign Application Priority Data

Sep. 24, 1985 [SE] Sweden .................................. 8504409

[51] Int. Cl.$^4$ ............................................ C07D 211/72
[52] U.S. Cl. ...................................... 546/345; 546/296
[58] Field of Search ................................ 546/296, 345

[56] References Cited

U.S. PATENT DOCUMENTS

| | | | |
|---|---|---|---|
| 3,960,869 | 6/1976 | Kyi | 546/296 |
| 4,544,750 | 10/1985 | Brandstrom et al. | 546/345 |

FOREIGN PATENT DOCUMENTS

| | | | |
|---|---|---|---|
| 140251 | 2/1980 | Fed. Rep. of Germany | 546/296 |
| 2123487 | 9/1972 | France | 546/296 |

OTHER PUBLICATIONS

Chemische Berichte, vol. 93, pp. 1849–1850 (1960).

*Primary Examiner*—Alan L. Rotman
*Assistant Examiner*—Robert C. Whittenbaugh
*Attorney, Agent, or Firm*—Brumbaugh, Graves, Donohue & Raymond

[57] ABSTRACT

A method for the preparation of 2,3,5-trimethylpyridine and some of its derivatives.

1 Claim, No Drawings

2,4-DICHLORO-3,5,6-TRIMETHYLPYRIDINE

DESCRIPTION

1. Technical Field

The present invention relates to a method for the preparation of 2,3,5-trimethylpyridine and some of its derivatives.

2. Background of the Invention 2,3,5-trimethylpyridine is a key intermediate in the synthesis of a class of compounds containing the structure element

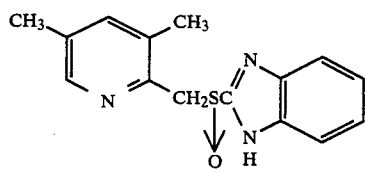

wherein the pyridine ring also is substituted in position 4 and wherein the benzimidazole structure may be substituted. These compounds are active as gastric secretion inhibitors as described e.g. in European patent No. 5129. One representative of this class, omeprazole, has the structural formula

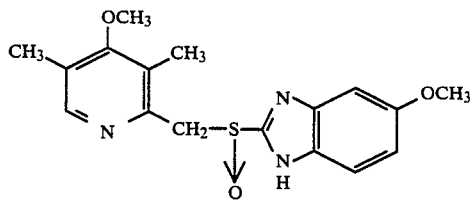

In European patent publication No. 0103553 the following synthetic route for the pyridine part of omeprazole is described:

Scheme 1

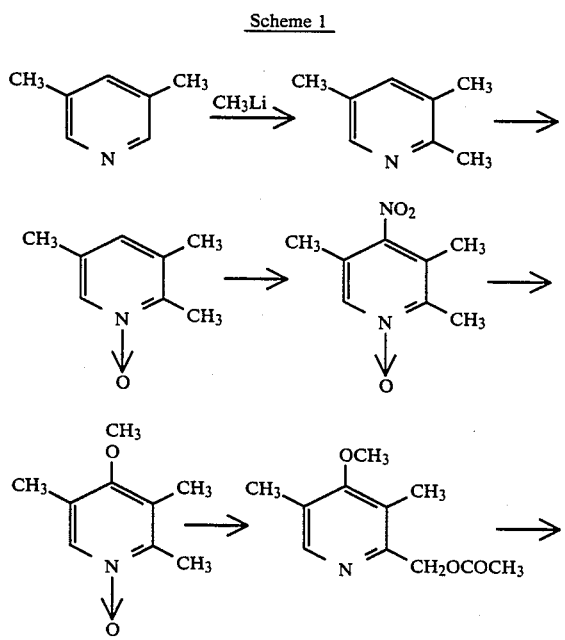

-continued
Scheme 1

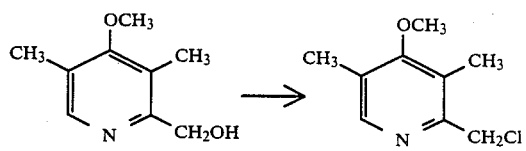

Since nitropyridines and their N-oxides are suspected carcinogens, it is desirable, for reasons of industrial hygiene, to develop routes not involving nitro compounds to the final compounds in Scheme 1.

DISCLOSURE OF THE INVENTION

The main idea underlying the present invention is that the pyridine skeleton is created from suitable aliphatic precursors, namely ethyl (monomethyl)acetoacetate and diethyl (monomethyl)malonate. In accordance with this part of the invention, ethyl (monomethyl)acetoacetate (I) is in a first step reacted with ammonia (II) according to the reaction formula

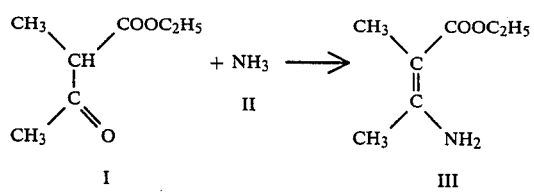

to the formation of ethyl-3-amino-2-methyl crotonate (III).

In this first step, the formation of the aminocrotonate, of the formula III, the ususal ammonia-water solution can be used, but the yield is in such case low (about 40%) and the reaction time is long. Preferably the reaction is carried out in pressure equipment with anhydrous liquid ammonia in 1.5-4 times molar excess of the required amount. The reaction temperature can be from 25°–100° C.

In a second step, the compound of the formula III is reacted with diethyl (monomethyl)malonate (IV) according to the reaction formula

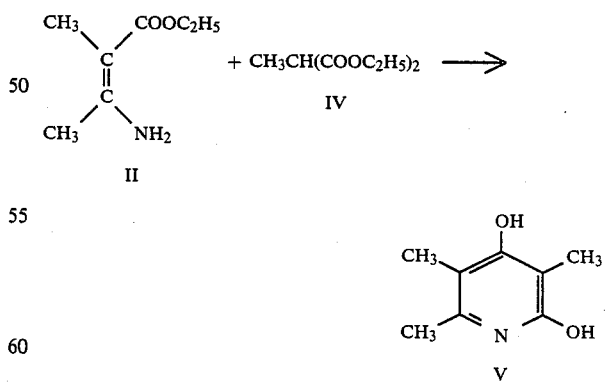

to the formation of 2,3,5-trimethyl-4,6-dihydroxypyridine (V).

This second step, leading to the formation of 2,3,5-trimethyldihydroxypyridine (V), can be performed in an inert solvent such as toluene and in the presence of a base. In a preferred embodiment, the best yield is obtained in the presence of an alkoxide such as $C_2H_5ONa$ in the corresponding alcohol $C_2H_5OH$ with 0–30% of toluene or similar aromatic solvent mixed into the solvent.

The compound 2,3,5-trimethyl-4,6-dihydroxypyridine (V) is novel and represents as such one aspect of the invention.

In a third step, the 2,3,5-trimethyl-4,6-dihydroxypyridine (V) is chlorinated to form 2,4-dichloro-3,5,6,-trimethylpyridine (VI) according to the reaction formula

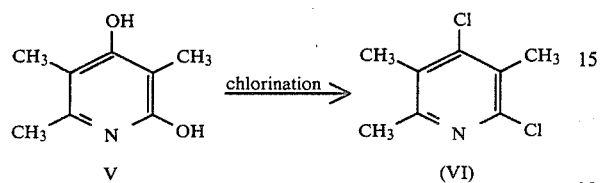

The chlorination of 2,3,5-trimethyl-4,6-dihydroxypyridine needs phosphoros oxychloride $POCl_3$ or $PCl_5$ or mixtures thereof and temperatures from 70°–190° C. to get high yields and pure product.

The compound 2,4-dichloro-3,5,6-trimethylpyridine (VI) is novel and represents as such one aspect of the invention.

In order to obtain 2,3,5-trimethylpyridine (VII) which is a useful starting material for preparing e.g. omeprazole as is outlined in Scheme 1, the compound 2,4-dichloro-3,5,6-trimethylpyridine (VI) is hydrogenerated in non-acidic, that is neutral or basic solution:

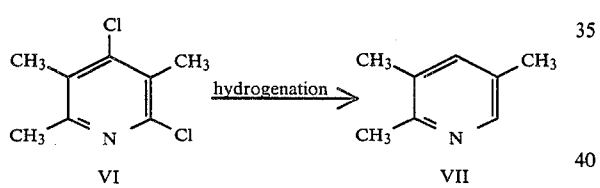

The hydrogenation can be carried out using e.g. palladium as catalyst. This reaction represents an additional aspect of the invention.

The reaction can also be performed with zinc in acidic medium as the reducing agent. These reactions represent an additional aspect of the invention.

In order to obtain 3,5-dimethyl-4-alkoxy-2-acetoxymethylpyridine (XIV) which with methoxy in position 4 is a useful intermediate in the preparation of omeprazole, the compound 2,4-dichloro-3,5,6-trimethylpyridine (VI) is in a first step hydrogenated in acidic medium to form 4-chloro-2,3,5-trimethylpyridine (VIII):

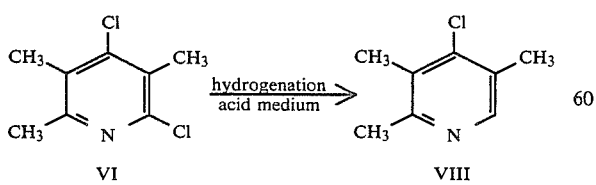

The hydrogenation is suitably carried out with palladium as catalyst and suitably in acetic acid or other acid-containing solvents. The hydrogen pressure is suitably from atmospheric to about 25 bar.

The 4-chloro substituent in the compound VIII can then in a second step be replaced with an alkoxy group containing 1-4 carbon atoms and oxidized to its N-oxide by either of two routes:

(a1) reacting 4-chloro-2,3,5-trimethylpyridine (VIII) with an alkoxide according to the formula

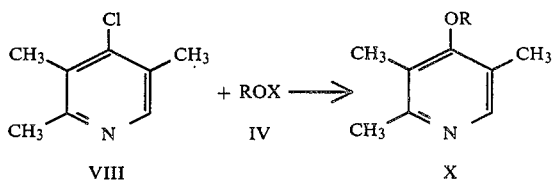

wherein R is an alkyl group containing 1-4 carbon atoms, and X is an alkali metal such as Na.

This replacement of the chlorine in 4-chloro-2,3,5-trimethyl pyridine with an alkoxy group by reaction with an alkoxide is suitably performed in an aprotic polar solvent, e.g. DMF, DMSO to obtain useful reaction rates. The methoxide ($R=OCH_3$) can also be formed in situ from DMSO containing methanol and solid potassium hydroxide.

(a2) oxidizing compound (X):

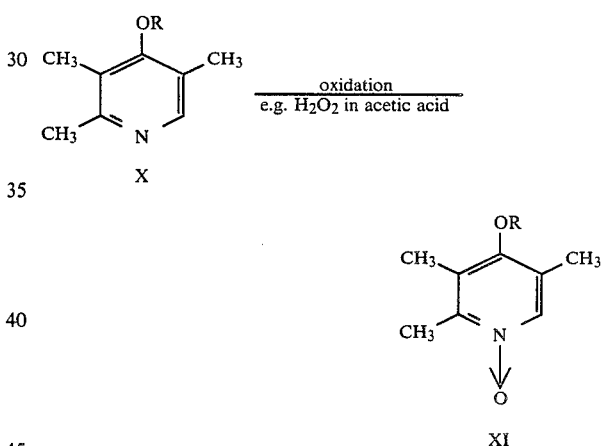

(b1) oxidizing compound VIII:

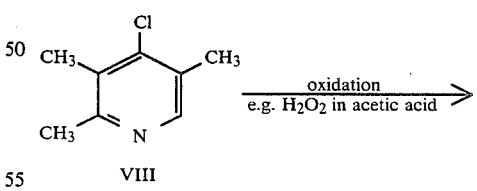

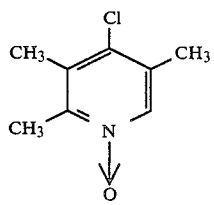

(b2) replacing the 4-chloro substituent in the compound XII with an alkoxy group containing 1-4 carbon atoms by reacting compound XII with an alkoxide ROX:

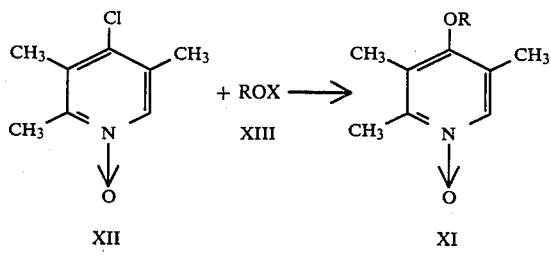

in which formulas R and X are as defined above.

The reaction b2 is suitably carried out in the alcohol corresponding to the alkoxide as solvent.

The reactions a1 and b1 represent part of the invention.

By the above methods, nitro-substituted compounds are avoided.

The compound 4-Cl -2,3,5-trimethylpyridine (XII) is novel and represents part of the invention.

Finally, in order to arrive at the 3,5-dimethyl-4-alkoxy-2-acetoxymethylpyridine (XIV) the compound XI is reacted with acetic anhydride:

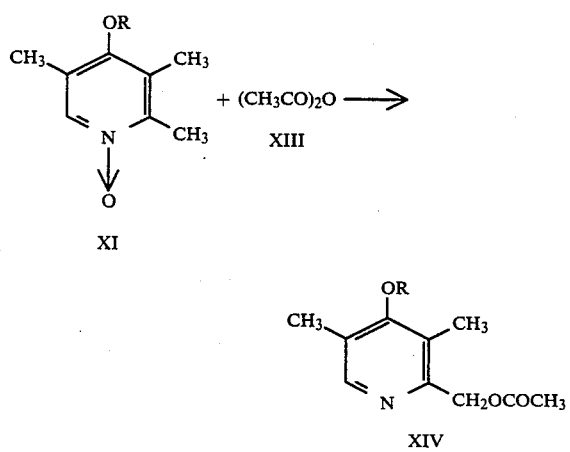

EXAMPLES

EXAMPLE 1

Preparation of ethyl-3-amino-2-methylcrotonate acid (III)

10 kg ethyl methylacetoacetate and 4 l abs. etanol was mixed in an autoclave and 3.4 kg of liquid ammonia was added. The mixture is stirred and the temperature gradually increased to 80° C. during 4 hrs. This temperature is maintained over night. The temperature is decreased to 40° C. and the excess ammonia is evaporated. Toluene (10 l) is added and the water is separated. The organic layer is dried by evaporation of toluene and alcohol. The yield is quantitative. The product is low melting solid.

$^1$H NMR: 3H, 1,25(t); 3H, 1,7(s); 3H, 1,9(s); 2H, 4,1(q). Solvent CDCl$_3$ ref TMS.

EXAMPLE 2 cl Preparation of 2,3,5-trimethyl-4,6-dihydroxypyridine (V)

1.77 kg (77 mol) sodium was dissolved in 26 l abs. ethanol and 4 l toluene. 13.1 kg (75 mol) diethyl methylmalonate was added and after 30 min all the crotonate from the previous step dissolved in 10 l toluene was added and the mixture refluxed for 44 hrs during which a precipitate was formed. 50 l water was added and the mixture stirred and heated to 40° C. until a two phase system was formed. The water layer was washed with some toluene. The water was neutralized with conc. hydrochloric acid to pH 7.1 and the precipitate was separated in a centrifuge and washed with water. Yield of dried product 8.7 kg. M.p. 260° C. (dec).

NMR: 6H, 1.9(s); 3H, 2,12(s) (DMSO-D$_6$ ref. TMS).

EXAMPLE 3

Preparation of 4,6-dichloro-2,3,5-trimethylpyridine (VI)

7.5 kg (49 mol) of phosphorus oxychloride 4,6-dihydroxy-2,3,5-trimethylpyridine and 12 l (20.1 kg, 131 mol) phosphorous oxychloride was mixed in an autoclave and is heated to 150° C. for 4 hrs. The mixture was allowed to cool down over night and was poured on 50 kg ice. The water solution was neutralized and the precipitated product was taken up in toluene. the toluene was washed with base and the toluene evaporated giving an oil that solidified on cooling. the yield of 4,6-dichloro-2,3,5-trimethylpyridine is 97%. M.P. 67°–68° C.

NMR: 3H, 2,2(s); 3H, 2,3(s); 3H, 2,4(s) (DMSO-D$_6$, ref TMS).

EXAMPLE 4

Preparation of 2,3,5-trimethylpyridine (VII)

20 g 4,6-dichloro-2,3,5 trimethylpyridine was dissolved in 150 ml ethanol and 1 g 10% Pd/C and 10 ml conc. aqueous ammonia. The hydrogenation was performed at 3 bar for 3 hrs when the calculated amount of hydrogen had been adsorbed. Evaporation of solvent gave the 2,3,5-trimethylpyridine.

EXAMPLE 5

Preparation of 2,3,5-trimethylpyridine (VII)

3,8 g (20 mmoles) of 4.6-dichloro-2,3,5-trimethylpyridine are dissolved in a small amount of ethanol and treated with 5 g of zinc powder. After addition of 10 ml of 2 N H$_2$SO$_4$, the mixture is refluxed for 1 hour. After cooling and filtering the solution is treated with NaOH to adjust a pH of 6. The precipitated zinc salts are removed by filtration and the filtrate is extracted three times with petrol ether. After drying and evaporation 2.0 g (83%) of 2,3,5-trimethylpyridine are obtained.

EXAMPLE 6

Preparation of 4-chloro-2,4,5-trimethylpyridine (VIII)

200 g 4,6-dichloro-2,3,5-trimethylpyridine dissolved in 300 ml ethanol and 40 ml conc. sulphuric acid. 2 g 10% Pd/C was used as catalyst. The hydrogen pressure was 2 bar and the hydrogenation was stopped when 1 equivalent of hydrogen had been consumed. After evaporation of alcohol and dilution with water and adjustment of pH to 2.1 the water was extracted with toluene. The toluene contains all starting material and 6-chloro-2,3,5-trimethylpyridine and the water phase 4-chloro-2,3,5-trimethylpyridine and 2,3,5-trimethylpyridine. The pH of the water phase is adjusted to 4.6 and extracted with toluene (3x100 ml). All 4-chloro-2,3,5-trimethylpyridine is in the toluene layer and the 2,3,5-trimethylpyridine in the water. Evaporation of the toluene gave 4-chloro-2,3,5-trimethylpyridine in 78% yield (liquid). NMR: 2×3H, 2,3; 3H, 2,5(s); 1H, 8,25(s). (CDCl₃)

EXAMPLE 7

Preparation of 4-methoxy-2,3,5-trimethylpyridine 60 g (0.39 mol) 4-chloro-2,3,5-trimethylpyridine and 21.7 g (0.40 mol) sodium methoxide and 180 ml dry dimethylsulfoxide was heated with stirring to 55°-60° C. for 8 hrs. The reaction mixture was diluted with 600 ml water and extracted with 3x100 ml toluene and the organic layer washed with 2x50 ml water. The organic phase was added to 200 ml water and pH adjusted to 4.1 with stirring. This process was repeated twice with 200 ml and 100 ml of water. The organic layer contained almost pure starting material. The combined water phase was made alkaline and extracted with 2×150 ml methylene chloride. Evaporation of solvent gave 40.7 g of almost pure 4-methoxy-2,3,5-trimethylpyridine. NMR: 2×3H, 2,2: 3H, 2,45(s); 3H, 3,75(s); 1H, 8,2(s). (CDCl₃)

EXAMPLE 8

Preparation of 4-chloro-2,3,5-trimethylpyridine N-oxide (XII)

11.3 g (72.8 mmol) 4-chloro-2,3,5-trimethylpyridine was dissolved in 50 ml acetic acid and heated to 60° C. and 6.2 ml (50% H₂O₂) was added slowly and the temperature maintained for several hours and finally increased to 90° for two hours. The solvent was evaporated and extracted from alkaline water with diethyl ether to remove unreacted starting material. The water phase was saturated with sodium chloride and extracted several times with methylene chloride. The methylene chloride was dried and evaporated to give 10.1 g of product. Yield 83%. M.p. 147°–148° C.
NMR: 3H, 2,3(s); 3H, 2,4(s); 3H, 2,55(s); 1H, 8,2(s) (CDCl₃, ref TMS).

EXAMPLE 9

Preparation of 4-methoxy-2,3,5-trimethylpyridine N-oxide via method a1)

0.86 g (5 mmol) 4-chloro-2,3,5-trimethylpyridine N-oxide and 8.5 ml 2M sodium methoxide was heated in a closed vessel to 70° C. for 16 hrs. Gave after work up 92% yield of 4-methoxy-2,3,5-trimethylpyridine N-oxide. Addition of 20% dimethylsulfoxide to the solvent increases the reaction rate but complicates the work up. The product was obtained as a waxy solid. NMR: 2×3H, 2,25; 3H, 2,5(s); 3H, 3,80(s); 1H, 8,2(s). (CDCl₃).

EXAMPLE 10

Preparation of 4-methoxy-2,3,5-trimethylpyridine N-oxide via method b1)

100 g 4-methoxy-2,3,5-trimethylpyridine was dissolved in 300 ml glacial acetic acid and 100 ml 50% hydrogenperoxide and stirred at 30° C. for 1 h. The temperature was gradually heated to 70° C. and was maintained for 5 hrs and the temperature increased to 90° C. and a small amount of Pd/C added to destroy excess hydrogenperoxide. After testing that the peroxide was destroyed the solvents were evaporated at reduced pressure. Toluene was added and stripped off to make the product free from water. After the product was dry most of the toluene was evaporated in vacuum. The 4-methoxy-2,3,5-trimethylpyridine N-oxide was diluted with acetic acid and used directly in the next step. The yield of N-oxide was 95%.
Partly crystalline m.p. 35° C.
NMR: 2×3H, 2,2; 3H, 2,5(s); 3H, 3,8(s); 1H, 8,15(s) (CDCl₃ ref TMS).

EXAMPLE 11

Preparation of 3,5-dimethyl-4-methoxy-2-acetoxymethyl 30 g 4-methoxy-2,3,5-trimethylpyridine N-oxide was dissolved in 70 ml of glacial acetic acid. This solution was added to 100 ml of acetic anhydride at 90° C. The mixture was heated to 120° C. and was maintained at this temperature for 1 h and then cooled to 30° C. Methanol was added to destroy excess of acetic anhydride. The solvents were evaporated to a viscous liquid and the crude acetate used directly in alkaline hydrolysis.
NMR: 3H, 2,1(s); 3H, 2,3(s); 3H, 3,8; 2H, 5,25(s); 1H, 8,35(s) (CDCl₃, ref TMS).

We claim:
1. A compound Compound selected from the group consisting of a compound compound having the formula

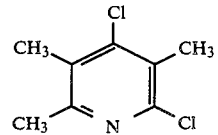

or the N-oxide thereof.

* * * * *

UNITED STATES PATENT AND TRADEMARK OFFICE
CERTIFICATE OF CORRECTION

PATENT NO. : 4,785,113

DATED : November 15, 1988

INVENTOR(S) : Hans Junek et al.

It is certified that error appears in the above-identified patent and that said Letters Patent is hereby corrected as shown below:

Column 8, line 40, delete "Compound"

Column 8, line 41, delete "compound" (2nd occurrence).

Signed and Sealed this

Twentieth Day of June, 1989

Attest:

DONALD J. QUIGG

Attesting Officer

Commissioner of Patents and Trademarks